(12) United States Patent
Lu et al.

(10) Patent No.: US 10,593,070 B2
(45) Date of Patent: Mar. 17, 2020

(54) MODEL-BASED SCATTER CORRECTION FOR COMPUTED TOMOGRAPHY

(71) Applicant: Toshiba Medical Systems Corporation, Otawara-shi (JP)

(72) Inventors: Yujie Lu, Vernon Hills, IL (US); Xiaohui Zhan, Vernon Hills, IL (US); Zhou Yu, Wilmette, IL (US); Richard Thompson, Hawthorn Woods, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 96 days.

(21) Appl. No.: 15/853,034

(22) Filed: Dec. 22, 2017

(65) Prior Publication Data
US 2019/0197740 A1 Jun. 27, 2019

(51) Int. Cl.
| | | |
|---|---|---|
| G06T 11/00 | (2006.01) | |
| A61B 6/03 | (2006.01) | |
| A61B 6/00 | (2006.01) | |
| G06T 7/11 | (2017.01) | |
| G06T 7/174 | (2017.01) | |

(52) U.S. Cl.
CPC ............ G06T 11/005 (2013.01); A61B 6/032 (2013.01); A61B 6/4291 (2013.01); A61B 6/4435 (2013.01); A61B 6/5205 (2013.01); G06T 7/11 (2017.01); G06T 7/174 (2017.01); A61B 6/5282 (2013.01); G06T 2207/10081 (2013.01); G06T 2207/20182 (2013.01); G06T 2207/30004 (2013.01)

(58) Field of Classification Search
CPC ........... G06T 7/11; G06T 7/174; A61B 6/032; A61B 6/4291; A61B 6/4435; A61B 6/5205
See application file for complete search history.

(56) References Cited

U.S. PATENT DOCUMENTS

| 6,256,367 B1 | 7/2001 | Vartanian |
|---|---|---|
| 2004/0030255 A1 | 2/2004 | Alfano et al. |

(Continued)

OTHER PUBLICATIONS

Zou et al., "A Physics-based Fast Approach to Scatter Correction for Large Cone Angle Computed Tomographic Systems," IEE Nuclear Science Symposium Conference Record, 2011.

(Continued)

*Primary Examiner* — Nirav G Patel
(74) *Attorney, Agent, or Firm* — Oblon, McClelland, Maier & Neustadt, L.L.P.

(57) ABSTRACT

A method and apparatus is provided to simulate and correct for scatter flux detected in a computed tomography (CT) scanner. The scatter flux from a bowtie filter and an anti-scatter grid are pre-calculated to generate respective scatter tables. Scatter from an imaged object is simulated for some views of a CT scan using a three-step radiative transfer equation (RTE) method. Using the simulated scatter flux from these views, an accelerated simulation method, such as a multiplicative method, an additive method, and a kernel-based method, can determine scatter flux for the remaining views. The spatial model for X-ray scatter from the object can be based on a reconstructed image of object, and can be segmented into organs and material components having different scatter cross-sections. A scatter model outside the imaging region can be extrapolated using low-dose scanning, a scout scan, and/or anatomical information.

19 Claims, 11 Drawing Sheets

(56) References Cited

U.S. PATENT DOCUMENTS

2006/0259282 A1    11/2006  Failla et al.
2018/0001806 A1     1/2018  Lu et al.
2018/0325485 A1*   11/2018  Maslowski .......... A61B 6/4085

OTHER PUBLICATIONS

Ohnesorge et al., "Efficient object scatter correction algorithm for third and fourth generation CT scanners," European Radiology, 9, 1999.
Sun et al., "Improved scatter correction using adaptive scatter kernel superposition," Physics in Medicine and Biology, 55, 2010.
Zbijewski et al., "Efficient Monte Carlo based scatter artifact reduction in cone-beam micro-CT," IEE Transactions on Medical Imaging, Aug. 2006.
Polundniowski et al., "An efficient Monte Carlo-based algorithm for scatter correction in keV cone-beam CT," Joint Department of Physics, Institute of Cancer Research and Royal Marsden NHS Foundation Trust, United Kingdom.
Sun et al., "Rapid Scatter Estimation for CBCT using the Boltzmann Transport Equation," SPIE vol. 9033, 2014.
Amit Joshi, et al., "Radiative Transport Based Frequency Domain Fluorescence Tomography", Apr. 21, 2008, Phys Med Biol., 53(8): 2069-2088. doi: 10.1088/0031-9155/53/8/005., 27 pages.

* cited by examiner

MODEL-BASED SCATTER CORRECTION FOR COMPUTED TOMOGRAPHY

FIELD

This disclosure relates to scatter correction of X-ray projection data, and, more particularly, to calculating scatter using pre-calculated tables of scatter for elements of the scanner and using accelerated scatter simulations including integrating a radiative transfer equation.

BACKGROUND

In general, an X-ray projection image contains many scattered radiation components. This scattered radiation can degrade the accuracy of computed tomography (CT) projection data for three-dimensional imaging using a two-dimensional detector. A two-dimensional detector, like a flat-panel detector used in an X-ray diagnostic apparatus, can use a scattered-radiation-removing grid (e.g., an anti-scatter grid) to suppress scattered radiation. The suppression of scattered radiation can be further improved by post processing the projection data using a scatter-correction algorithm. Scattered radiation correction can be advantageous for extracting low-contrast information, such as when imaging soft tissue.

An X-ray beam in the presence of a scattering object can be modeled as a primary X-ray beam P(x, y) and a scattered X-ray beam S(x, y), wherein the projection data T(x, y) is a composite of these two:

$$T(x,y)=P(x,y)+S(x,y).$$

To correct for the scatter, a kernel-based method can be used. Alternatively, a scatter simulation can be used to compute the scatter based on information of the intervening object responsible for the scatter. Given the simulated scatter, the measured projection data can be corrected by subtracting the simulated scatter, leaving the primary beam for CT reconstruction of an image.

Inefficient scatter simulation and compensation significantly affects imaging quality including poor image contrast, artifact generation, and large errors in CT projection data. In cone-beam CT configured in a wide-beam geometry, scatter correction can become even more important for reconstructing high quality images. Besides hardware-based scatter rejection such as anti-scatter grids and air gaps, approximated-convolution models with experimental parameter calibration is common in current commercial CT. However, for practical clinical application, significant errors (typical 20-40HU) persist when performing scatter correction using approximated-convolution models. Improved methods of correcting scatter in X-ray CT are desired. Further, improvements reducing the computational load and time for scatter correction while maintaining or even improving its accuracy are desired.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
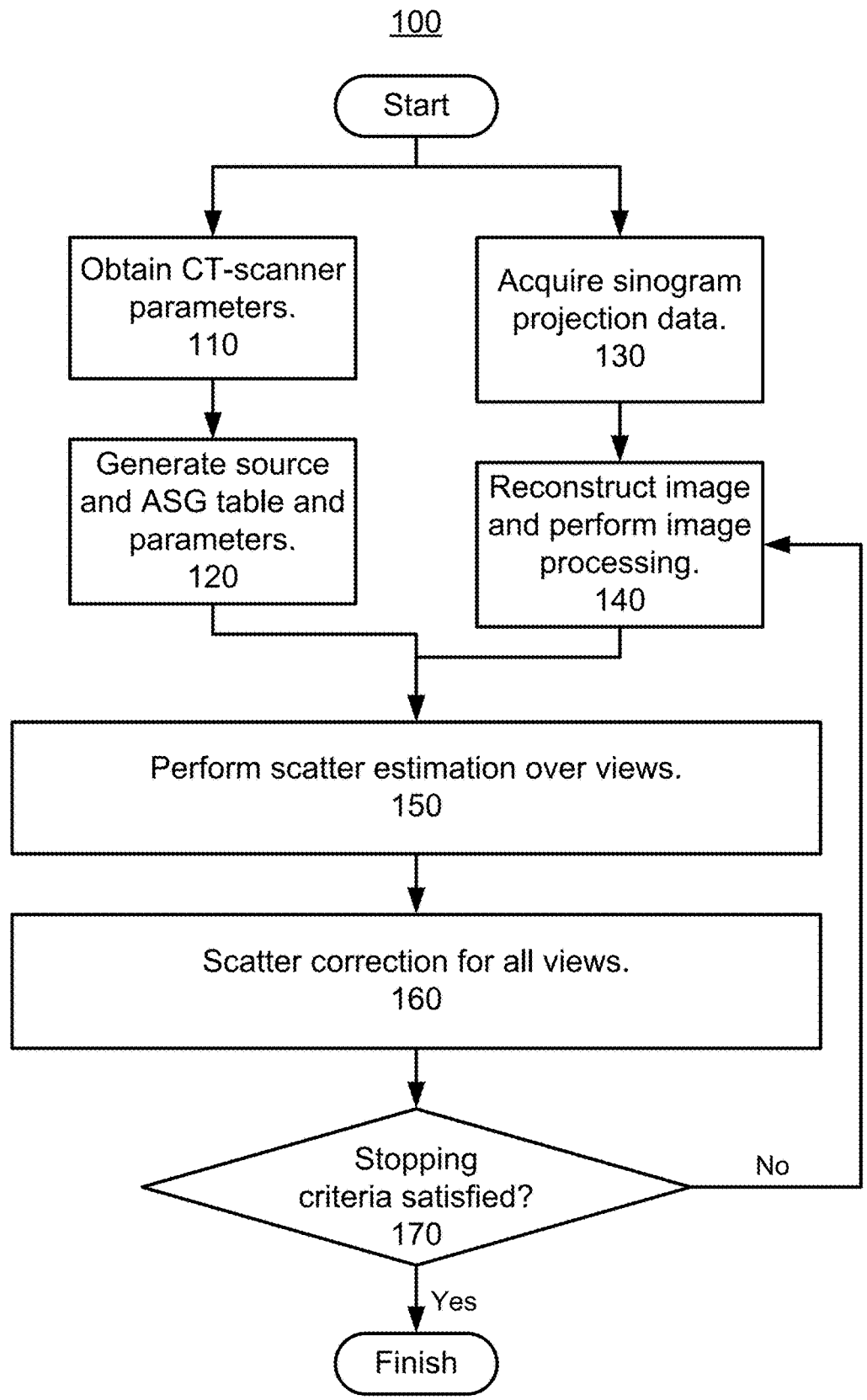
FIG. 1 shows a flow diagram of a method of correcting scatter from projection data using a scatter simulation, according to one implementation.

Hardware-based solutions to the scatter-correction problem, especially anti-scatter grids (ASGs), can effectively reject scatter photons in computed tomography (CT), but hardware solutions alone can significantly increase the scanner cost and potentially reduce the primary signal. Thus, post-processing methods to correct for scatter play an important role in scatter correction to achieve good performance while maintaining low cost. Convolution-based methods are known to correct scatter, but model-based approaches show promise for the future. For example, patent application Ser. No. 15/210,657, incorporated herein by reference in its entirety, describes a radiation transfer equation (RTE) simulation method to correct scatter in X-ray CT data. The methods described herein provide an improvement over the simulation methods of patent application Ser. No. 15/210,657.

For example, the methods described herein efficiently incorporate models for a bowtie filter and for ASGs into the scatter simulation. The scatter simulation should ideally account for all elements interacting with the X-rays between the sources and detector, but some of these elements do not change between scans and views (i.e., projection angles within a scan). For example, a bowtie filter and an anti-scatter grid (ASG) remain in a constant arrangement with respect to the X-ray source and detectors as the CT scanner rotates through the various views (i.e., projection angles) of the CT scan. Moreover, in contrast to the scatter model for a patient being imaged, which changes each scan because different patients are being imaged in different scans, the bowtie filter and ASG can remain constant between scans with the practical effect that the scatter model can be pre-calculated once and then reused for all subsequent scans.

Taking advantage of this insight, the methods herein provide efficient mechanisms to simulate and correct for scatter from the unchanging elements. For example, for the unchanging elements between the X-ray source and detector, lookup tables can be pre-calculated once in anticipation of future scatter simulations. Then the lookup tables can be reused during each subsequent simulation, saving significant computation resources and time. Thus, the lookup tables can advantageously be used rather than repeating the RTE calculation of the bowtie filter and ASG for each scan. Consequently, the methods described herein provide improved simulations that use fewer calculations for bowtie and anti-scatter grid (ASG), which improvements are realized through recognizing that conventional CT geometries have unchanging elements that contribute to the scatter. Additionally, because these pre-calculations are one-time events, these pre-calculations can be performed at higher resolution and accuracy to provide improved scatter correction without affecting the computational cost for subsequent scatter simulations and corrections.

For example, the methods described herein provide a new method/framework for scatter correction of CT projection data using an RTE simulation, which among other things, is better able to handle complex geometry and multiple materials and perform patient-specific scatter correction, especially when compared and contrasted with pure convolution methods. When contrasted with Monte Carlo (MC) methods, the methods described herein provide scatter simulations free from shot noise.

Accordingly, without sacrificing precision or increasing noise, as is the case for other methods, the methods described herein provide fast simulations for scatter correction. Additionally, in contrast to other RTE-based methods, the method described herein do not require two-pass scatter correction. And as mentioned above, the bowtie-based virtual-surface source and ASG table can be pre-calculated to improve the accuracy and efficiency of the scatter correction. Finally, as described below, the methods described herein provide a novel scanning protocol to account for scatter extending into an unscanned region, further improving the accuracy and efficiency of scatter correction.

The improvements of the methods described herein can be understood by contrasting them with other methods. For example, convolution-based methods can estimate scatter profiles with conventional kernel and primary signal. The accuracy of the kernel directly affects the performance of these methods. However, kernel-based methods have limited ability to represent scatter from objects having complex shapes and/or multiple materials can be difficult. In contrast, model-based approaches can perform patient-specific scatter correction, by using a prior imaging information and precise simulation of physical scatter processes. Although Monte Carlo methods have been the gold standard for scatter simulation because, when allowed unlimited time, they provide precise scatter simulations, Monte Carlo methods have an inherent trade-off between accuracy and speed. The accuracy of Monte Carlo methods depends on using a large number of simulated photons to overcome the natural simulated noise resulting from their discrete and statistical nature. Unfortunately, simulating more photons increases the amount of computations and increases the simulation time. In contrast, scatter simulation using the deterministic radiative transfer equation (RTE) potentially provides a noise-free solution with fast simulation speed. Further, compared to finite-element discrete ordinate methods, the integral spherical harmonics method for RTE scatter simulation can provide fast and a precise ray-effect-free scatter solution.

Referring now to the drawings, wherein like reference numerals designate identical or corresponding parts throughout the several views, FIG. 1 shows a flow diagram of a method 100 for correcting scatter in projection data.

In step 110 of method 100, various parameters relevant to the CT scanner are obtained. For example, parameters relevant to the CT scanner can include information of the X-ray source spectrum, the CT geometry, dimensions of the ASG, detector information, and various calibrations. These parameters can be used in determining the scatter correction. For example, different voltages across an X-ray tube can produce different X-ray spectra, and differences in the X-ray spectra can in turn affect the scatter and attenuation.

In step 120 of method 100, tables and parameters are generated for the X-ray source and the ASG. For example, as described below, the acceptance angle of the ASG can depend on the geometry of the ASG (e.g., a taller ASG would have a narrower acceptance angle than a shorter ASG having views with the same spacing). Thus, the tables and parameters can be tailored to the particular geometry and parameters of the CT scanner.

In step 130 of method 100, projection data is acquired by scanning the CT scanner through a series of projection angles to generate a sinogram of an object OBJ. These projection angles can also be referred to as views. The object OBJ can be a patient or a phantom, for example.

In step 140 of method 100, an image is reconstructed from the projection data. For example, the image can be reconstructed using one of a filtered back-projection method, an iterative reconstruction method (e.g., an algebraic reconstruction technique (ART) method or a total variation minimization regularization method), a Fourier-transform-based method (e.g., direct Fourier method), and a statistical method (e.g., a maximum-likelihood expectation-maximization algorithm based method). In certain implementations, the image can be reconstructed using an iterative reconstruction (IR) method, and can use order-subsets (OS), Nesterov acceleration, separable paraboloidal surrogate (SPS), or any known accelerator techniques. Also, the image can be reconstructed using an iterative reconstruction (IR) method to optimize any known cost function and using any known regularizers. In certain implementations, a scatter-correction method (e.g., a kernel-based method) that does not require a model for the imaged object OBJ can be applied to the projection data prior to performing the image-reconstruction.

In step 150 of method 100, scatter estimation is performed using any of the methods described herein including the multiplicative method, the additive method, or the kernel-based method described below. Further, as described below, these three methods can use an RTE simulation method, such as method 200 described below.

In addition to reconstructing the image, various image and signal processing operations can be performed on the reconstructed image. For example, smoothing or denoising operations can be performed to reduce noise. Also, for projection data having multiple energy components, material decomposition can be performed to differentiate soft tissues from bone, for example. Material decomposition can be beneficial for scatter correction because different materials can exhibit different scatter cross-sections, attenuation coefficients, and energy/spectral dependences.

In step 160 of method 100, scatter correction is performed to remove the scatter contribution from the total projection data and recover the primary beam.

In step 170 of method 100, in certain implementations, steps 140, 150, and 160 can be repeated iteratively until the solution converges to a final solution. Otherwise, step 170 can be omitted. If step 170 is not omitted, then, for each iteration, the primary beam extracted in step 160 provides a more accurate source of sinogram data to perform reconstruction of the image in step 140, than the sinogram data used in the previous iteration. And the image reconstructed from better sinogram data provides, in turn, a better estimate of the X-ray scatter. Thus, successive iterations can progressively converge to the optimal scatter correction and optimal reconstructed image. The stopping criteria can include a maximum number of iterations and/or a measure of the change between iterations (e.g., a p-norm of a difference between the simulated scatter or a difference between the reconstructed images for successive iterations) falling below a predefined threshold.

As mentioned above, the multiplicative, additive, and kernel-based methods of scatter correction can be used to simulate the scatter from the reconstructed image. Each of these methods uses, in some manner, an RTE simulation to achieve its results. Accordingly, a general description of an RTE simulation method (i.e., method 200) is provided, and then description of the multiplicative, additive, and kernel-based methods are provided.

Figure 2:
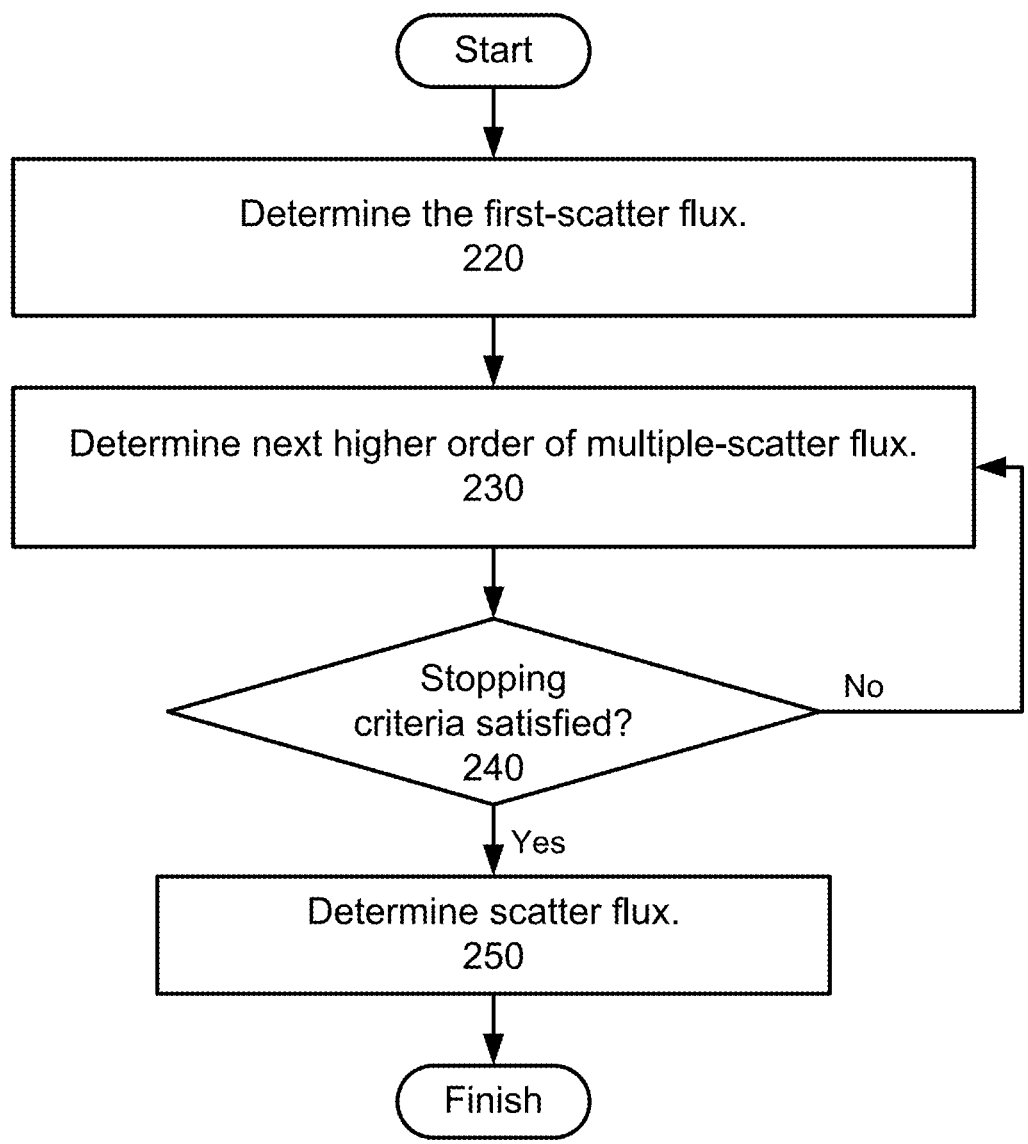
FIG. 2 shows a flow diagram of a method of performing the scatter simulation using a radiative transfer equation, according to one implementation.
Figure 3:
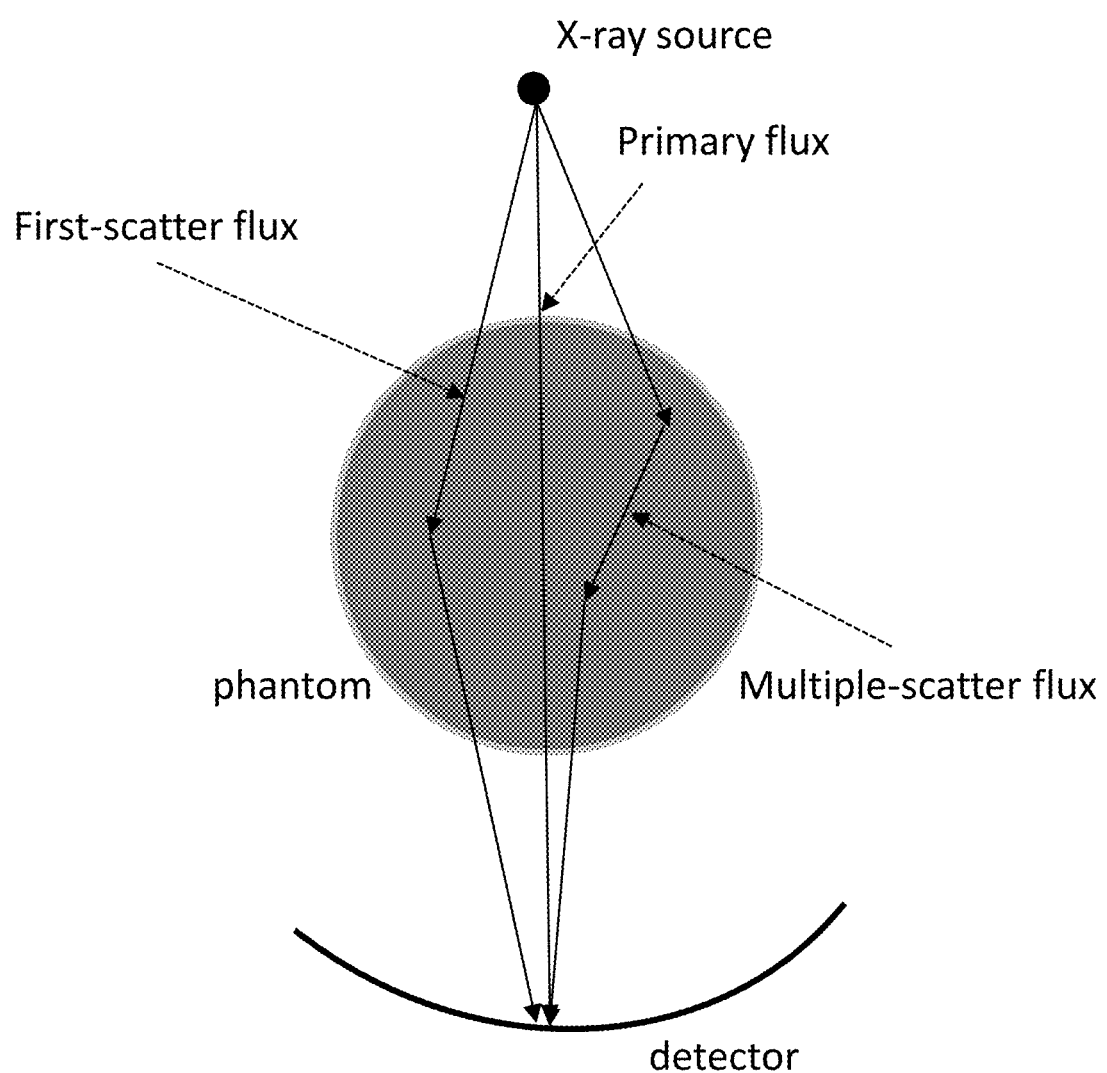
FIG. 3 shows a diagram of first-scatter X-rays and multiple-scatter X-rays detected at a detector, according to one implementation.

FIG. 2 shows a flow diagram of a method 200 for simulating scatter using a three-step integral formulation of the RTE with spherical harmonics. FIG. 3 shows a diagram of the scatter process in which the primary flux is transmitted with attenuation through an object OBJ to a detector at which the primary and scatter flux are detected. As shown in FIG. 3, the object can be a phantom, or, in clinical applications, the object can be a patient. The primary flux includes the X-rays that are not scattered. In addition to detecting the primary flux, the detector also detects first-scatter flux, which includes X-rays that have undergone a single scattering event. Further, the detector also detects multiple-scatter flux, which includes X-rays that have been scattered multiple times.

As shown in FIG. 3, a complete physical scatter model of the scattered X-ray flux includes both the first-scatter flux and multi-scatter flux. This physical model can be expressed using a radiative transfer equation (RTE) given by $$\hat{\Omega}\cdot\nabla\psi(\vec{r},E,\hat{\Omega})+\mu(\vec{r},E)\psi(\vec{r},E,\hat{\Omega})=\iint d\hat{\Omega}'dE'f(\vec{r},E,E',\hat{\Omega}\cdot\hat{\Omega}')\psi(\vec{r},E,\hat{\Omega}'),$$

which is subject to the boundary condition $$\psi(\vec{r}_c,E,\hat{\Omega})=\psi_c(\vec{r}_c,E,\hat{\Omega}), \text{ for } \hat{n}\cdot\hat{\Omega}<0,$$

wherein $\psi(\vec{r}, E, \hat{\Omega})$ is the specific intensity of photon flux at point $\vec{r}$, E is an energy, and $\hat{\Omega}$ is unit vector in the direction of propagation of the photon flux. In the boundary condition, the intensity $\psi_c(\vec{r}_c, E, \hat{\Omega})$ depends on the X-ray source and (if a bowtie filter is used to collimator the X-ray source) on the bowtie scattering. The vector $\vec{r}^c$ indicates a point on the surface of the object, $\hat{n}$ is the normal vector to the boundary surface, and $f(\vec{r}', E, E', \hat{\Omega}\cdot\hat{\Omega}')$ is the scatter cross-section, which includes both Compton and Rayleigh scattering.

The method described herein solves the above RTE by subdividing the RTE into three simpler integral problems in order to obtain precise, but straightforward scatter simulation for CT scatter compensation. This is achieved by first rewriting the above RTE as the integral equation $$\psi(\vec{r}, E, \hat{\Omega}) = \psi_c(\vec{r}_c, E, \hat{\Omega})\exp\left[\int_{\vec{r}_c}^{\vec{r}} d\vec{r}'' \mu(\vec{r}'', E)\right] + \int_{\vec{r}_c}^{\vec{r}} d\vec{r}' \iint d\hat{\Omega}' dE' f(\vec{r}', E, E', \hat{\Omega}\cdot\hat{\Omega}') \psi(\vec{r}', E', \hat{\Omega}')\exp\left[-\int_{\vec{r}'}^{\vec{r}} d\vec{r}'' \mu(\vec{r}'', E')\right],$$

wherein the variable $\mu(\vec{r}, E)$ represents the attenuation coefficient at point $\vec{r}$ of X-rays having energy E.

As indicated in FIG. 3, the flux can be grouped into three components: (i) the primary flux, (ii) the first-scatter flux, and (iii) the multiple-scatter flux. Method 200 is organized to solve the integral equation representation of the RTE in steps corresponding to the above-identified three respective components of the flux. The RTE can be separated into at least two components (i.e., a scatter flux and a primary flux). Accordingly, given the primary flux $\psi_0(\vec{r}', E', \hat{\Omega}')$, the scatter flux $\psi_s(\vec{r}, E, \hat{\Omega})$ can be calculated by the integral expression $$\psi_s(\vec{r}, E, \hat{\Omega}) = \int_{\vec{r}_c}^{\vec{r}} d\vec{r}' \iint d\hat{\Omega}' dE' f(\vec{r}', E, E', \hat{\Omega}\cdot\hat{\Omega}')[\psi_s(\vec{r}', E', \hat{\Omega}') + \psi_0(\vec{r}', E', \hat{\Omega}')] \exp\left[-\int_{\vec{r}'}^{\vec{r}} d\vec{r}'' \mu(\vec{r}'', E')\right],$$

wherein the primary flux can be calculated by integrating the attenuation of the X-ray flux transmitted through the boundary $\psi_c(\vec{r}_c, E, \hat{\Omega})$ as expressed by the equation $$\psi_0(\vec{r}, E, \hat{\Omega}) = \psi_c(\vec{r}_c, E, \hat{\Omega})\exp\left[-\int_{\vec{r}_c}^{\vec{r}} d\vec{r}'' \mu(\vec{r}'', E')\right].$$

The integral equation for the scatter flux $\psi_s(\vec{r}, E, \hat{\Omega})$ can be further subdivided into a first scatter component $\psi_1(\vec{r}, E, l, m)$ and a multiple scatter component $\psi_s^k(\vec{r}, E, l, m)$ corresponding respectively to steps 220 and 230, which are described below.

In step 220 of method 200, the first-scatter flux is calculated. The first-scatter flux can be calculated by a discretized integral formula, which is given by $$\psi_1(\vec{r}, E, l, m) = \iiint d^3\vec{r}' \exp\left[-\int_{\vec{r}'}^{\vec{r}} d\vec{r}'' \mu(\vec{r}'', E')\right]\frac{1}{|\vec{r}-\vec{r}'|^2} Y_{lm}^*(\hat{\Omega}) \times \int dE' f(\vec{r}', E, E', \hat{\Omega}\cdot\hat{\Omega}')\psi_c(\vec{r}_c, E', \hat{\Omega}')\exp\left[-\int_{\vec{r}_c}^{\vec{r}'} d\vec{r}'' \mu(\vec{r}'', E')\right],$$

wherein $Y_{lm}^*(\hat{\Omega})$ is the complex conjugation of a spherical harmonic function of degree l and order m, and $\psi_1(\vec{r}, E, lm)$ is the intensity of the first-scatter flux in the spherical-harmonics domain. The spherical harmonics can be given by $$Y_{lm}(\hat{\Omega}) = Y_{lm}(\theta, \phi)$$
$$= N\exp(im\phi)P_l^m(\cos\theta),$$

wherein $Y_{lm}(\hat{\Omega})$ a spherical harmonic function of degree l and order m, $P_l^m$ is an associated Legendre polynomial, N is a normalization constant, and $\theta$ and $\phi$ represent colatitude and longitude, respectively.

Different materials, such as bone and water, have different scattering cross-sections with different angular dependence depending on their atomic constituents. Also, the magnitude of the scatter cross-section can depend on the density of material components at the point $\vec{r}$'. Thus, the physical model, such as the physical model shown in FIG. 3, can be decomposed into material components using a material decomposition to determine the density of various material components as a function of position, and the position-dependent scatter cross-section can be obtained from the spatial density map of the material components. The position-dependent X-ray scatter cross-section can be obtained as a linear superposition of respective products between the volume pixel (i.e., voxel) density ratios of the material components of the material decomposition and pre-calculated scatter cross-sections corresponding to the respective material components.

In one non-limiting example, the material decomposition can be performed using dual-energy CT. Also, another option for the material decomposition is to use a threshold and region growing method that infers regions corresponding to material components by the attenuation of the voxels (e.g., voxels having a attenuation value above a predefined threshold in Hounsfield Units are determined to be bone).

In step 230 of method 200, the higher-order scatter terms are calculated. Whereas the first-scatter flux includes only X-ray photons that have been scattered one time, the $k^{th}$-order scatter term includes X-ray photons that have been scattered k times. After the first-scatter flux is calculated, the flux of multiple scatters can be calculated using a discretized integral spherical harmonics formula, which is given by $$\psi_s^{k+1}(\vec{r}, E, l, m) =$$
$$\psi_1(\vec{r}, E, l, m) + \int\int\int d^3\vec{r}' \exp\left[-\int_{\vec{r}'}^{\vec{r}} d\vec{r}'' \mu(\vec{r}'', E')\right]\frac{1}{|\vec{r}-\vec{r}'|^2}$$
$$Y_{lm}^*(\hat{\Omega}) \times \sum_{E'}\sum_{\bar{l}} f(\vec{r}', E, E', \bar{l})\sum_{\bar{m}} Y_{\bar{l}\bar{m}}(\hat{\Omega})\psi_s^k(\vec{r}', E', \bar{l}, \bar{m}),$$

wherein $\psi_s^{k+1}(\vec{r}, E, lm)$ and $\psi_s^k(\vec{r}', E', \bar{l}m)$ are the intensity of the flux for multiple scatter including all scatter events up to order k+1 and order k respectively and $f(\vec{r}', E, E', \bar{l})$ is the $\bar{l}$-th coefficient when the scatter cross-section is expanded using the Legendre polynomials. By defining the operator A as $$A = \int\int\int d^3\vec{r}' \exp\left[-\int_{\vec{r}'}^{\vec{r}} d\vec{r}'' \mu(\vec{r}'', E')\right]$$
$$\frac{1}{|\vec{r}-\vec{r}'|^2}Y_{lm}^*(\hat{\Omega})\sum_{E'}\sum_{\bar{l}} f(\vec{r}', E, E', \bar{l})\sum_{\bar{m}} Y_{\bar{l}\bar{m}}(\hat{\Omega}),$$

the above-defined iterative formula can be more simply expressed as $$\psi_s^{k+1} = A\omega_s^k + \psi_1.$$

In step 240 of method 200, a stopping criteria is assessed to determine whether approximation up to order k is sufficiently accurate. That is, whether scattering accounted for by the above-defined iterative multiple-scatter calculation when calculated up to order k provides a predefined stopping criteria, e.g., related to the accuracy requirements for the scatter correction of a given clinical application. In certain implementations, the stopping criteria can be satisfied when $$\frac{|\psi_s^{k+1} - \psi_s^k|}{\psi_s^k} \leq \epsilon,$$

wherein $\epsilon$ is a predefined threshold. Further, the stopping criteria can be satisfied when a maximum value for k (i.e., a maximum number of iterations) has been reached. If the stopping criteria are satisfied, then method 200 proceeds from step 240 to step 250. Otherwise, step 230 is repeated for the next higher order of multiple scattering.

In step 250 of method 200, the flux at the detector is determined. After calculating the flux of multiple scatters, the above results can be combined to calculate the scatter flux intensity at the detectors $\Phi_s(\vec{r}_D, E)$, which is given by $$\Phi_s(\vec{r}_D, E) =$$
$$\int\int\int d^3r' \frac{1}{|\vec{r}_D-\vec{r}'|^2}\int dE' \sum_{l',m'} f(\vec{r}', E, E', l')Y_{l'm'}(\hat{\Omega})\psi_s$$
$$(\vec{r}', E', l'm') \times \exp\left[-\int_{\vec{r}'}^{\vec{r}_c} d\vec{r}'' \mu(\vec{r}'', E)\right] +$$
$$\int\int\int d^3r' R_{ASG}(E, \hat{\Omega})\frac{1}{|\vec{r}_D-\vec{r}'|^2}\int dE' f(\vec{r}', E, E',$$
$$\hat{\Omega}\cdot\hat{\Omega}')\times\psi_c(\vec{r}_c, E', \hat{\Omega}')\exp\left[-\int_{\vec{r}_0}^{\vec{r}'} d\vec{r}''\right]$$
$$\mu(\vec{r}'', E)\left]\exp\left[-\int_{\vec{r}'}^{\vec{r}_c} d\vec{r}'' \mu(\vec{r}'', E)\right],$$

wherein $R_{ASG}(E, \hat{\Omega})$ is the factor accounting for the effects of the anti-scatter grid. $R_{ASG}(E, \hat{\Omega})$ is dependent only on the arrangement and configuration of the anti-scatter grids, and, therefore, can be precomputed and stored for the configuration of the anti-scatter grids. $R_{ASG}(E, \hat{\Omega})$ can be precomputed using any known method, including any known analytical approach, Monte Carlo method, or RTE method. When no anti-scatter grid is used, $R_{ASG}(E, \hat{\Omega})$ can be replaced by a constant value of one.

Figure 4:
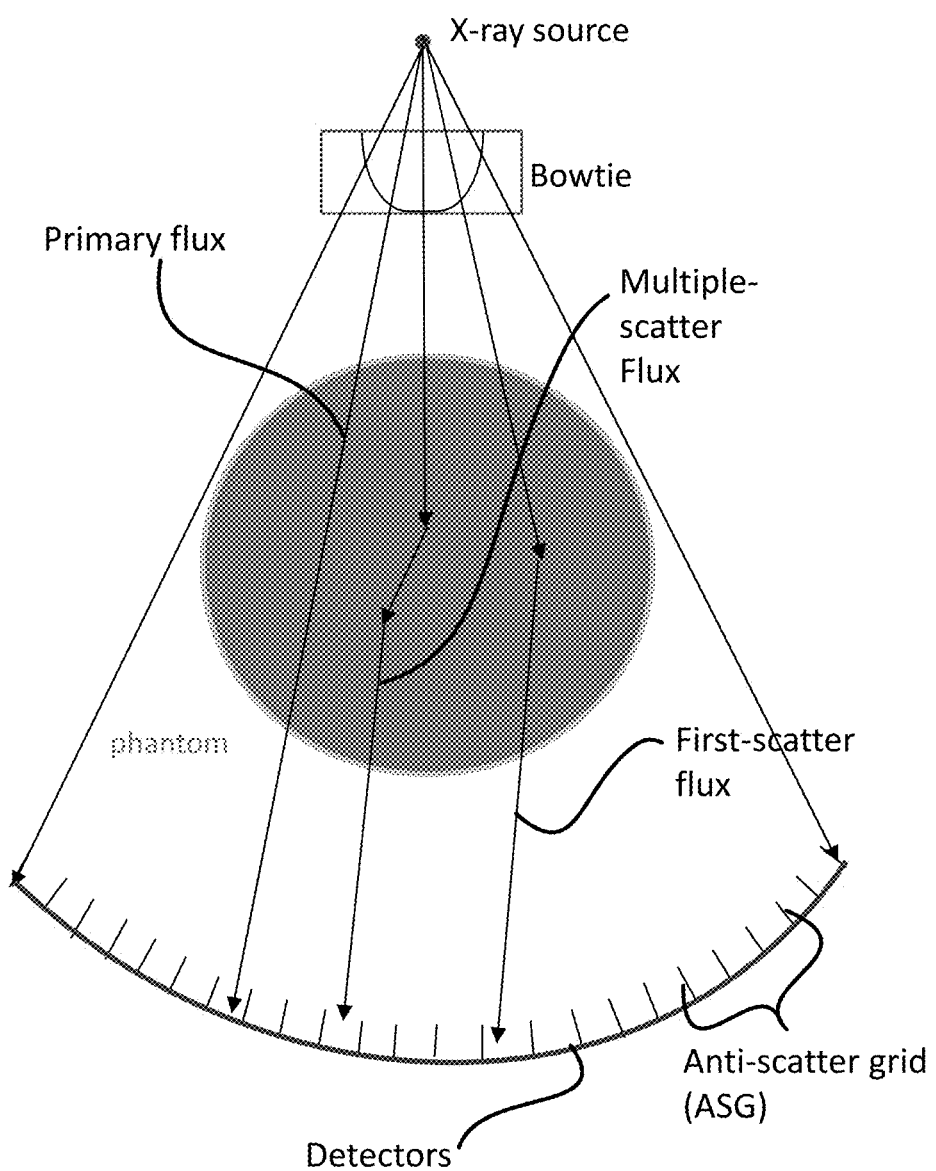
FIG. 4 shows a diagram of X-ray scatter in a computed tomography (CT) scanner having an anti-scatter grid (ASG) and a bowtie filter, according to one implementation.

FIG. 4 shows a simplified diagram of a path of X-rays in a CT scanner, including a bowtie filter and an ASG. As discussed above, a lookup table can be generated to express the simulated scatter and attenuation effects of the bowtie filter and the ASG on the X-rays. These lookup tables reduce the number of calculations to be performed when simulating the X-ray scatter. As shown in FIG. 4, the CT scanner includes an X-ray source, bowtie filter, anti-scatter grid (ASG), and detectors. The detectors detect total flux including primary and scatter flux, and the scatter correction method uses a scatter model to estimate the scatter flux based on the measured total flux, and then uses the scatter flux to extract the primary flux from the measured total flux before reconstructing an image from the extracted primary flux.

Figure 5:
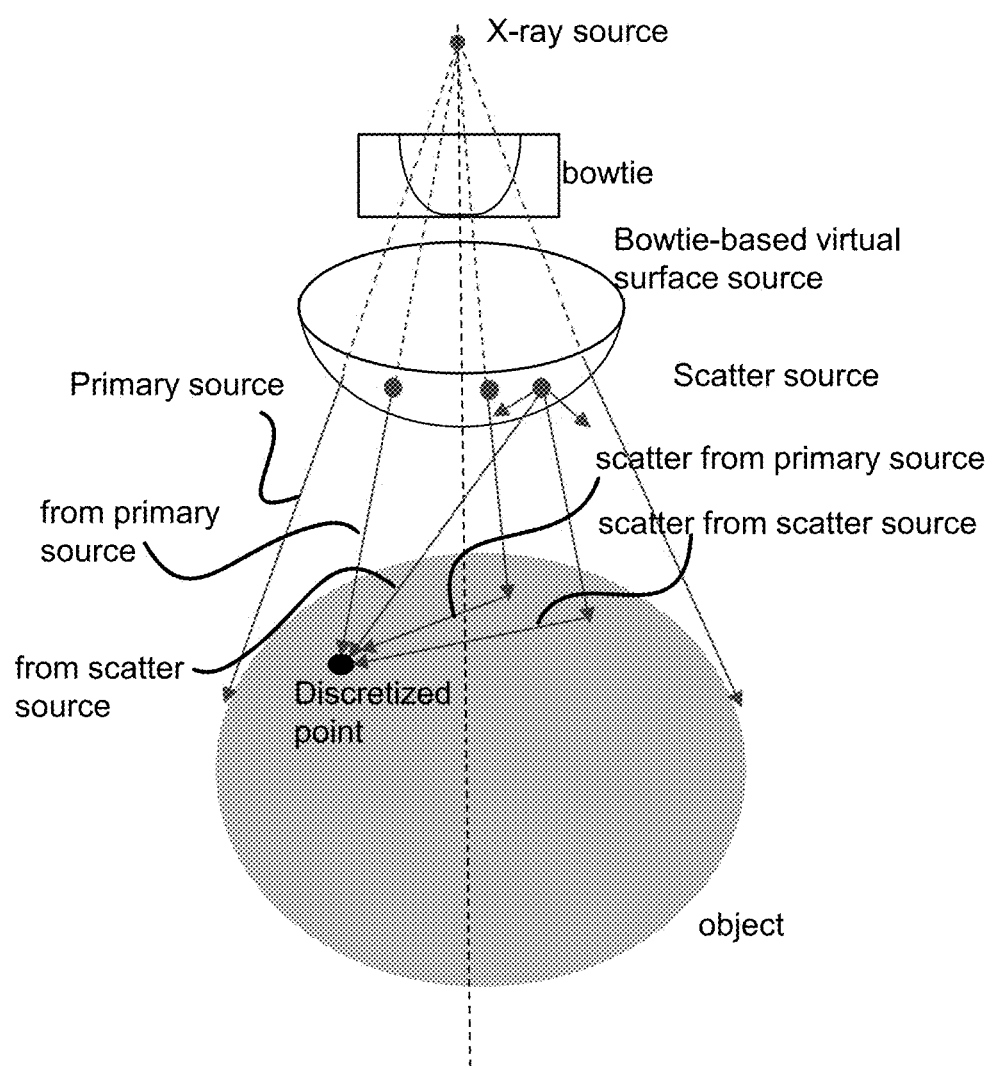
FIG. 5 shows a diagram of X-ray scatter from a bowtie filter being mapped to a virtual-surface source, which is represented in a table, according to one implementation.

FIG. 5 shows a diagram illustrating how the distributed scatter effects can be represented as a lumped parameter on a bowtie-based virtual scatter surface. The bowtie-based virtual-surface source simplifies the simulation by mapping the primary beam representing the X-ray source before the bowtie filter, which can exhibit spatial, angular, and energy dependences, to a virtual X-ray source emanating from the virtual-surface that represents the attenuated primary beam and scatter flux from the bowtie filter.

An X-ray source in a practical CT scanner can have a wide energy spectrum, and Compton scattering, which is the dominant scattering mechanism in biological tissue, can induce energy change (e.g., the energy of the scatter X-ray is less than the incident X-ray). In order to optimize the dose in a CT scanner, a bowtie can be used, resulting in an angle-dependent X-ray spectrum. In addition, the scatter flux generated from bowtie can affect the imaging quality especially at the boundary of the scanned object. In most CT scanners, the bowtie position relative to X-ray source is fixed, regardless of the view (i.e., projection angle). Accordingly, in order to improve the simulation efficiency, a bowtie-based virtual-surface source method can be used simplify the scatter simulation.

A virtual surface is chosen to represent the bowtie-based source. FIG. 5 shows a non-limiting example in which the virtual surface is a half-sphere. Two tables can be generated to respectively represent the primary and scatter beams exiting the virtual surface (i.e., the bowtie source can be bifurcated into a primary source and a bowtie scatter source). The primary source is a function of the cone and fan angles of X-ray source. The bowtie scatter source is also a function of cone and fan angles, but also depends on the scatter angle, which can be described by polar and azimuth angles.

The lookup table translates the beam from X-ray source incident on the bowtie filter to the virtual source exiting from the virtual-surface. Thus, bowtie-based virtual-surface source can be treated as the source, and additional consideration of the bowtie filter can be omitted from the scatter simulation. Consequently, the scatter simulation of the combination of the bowtie filter together with the object OBJ reduces to calculating for respective discretised points in the object OBJ the scatter due to incoming rays coming from the virtual surface (i.e., the primary and scatter beams from the virtual surface) and from scatter coming from other discretised points in the object OBJ (e.g., the first-scatter flux and multiple-scatter flux calculated respectively in steps 220 and 230 of method 200).

In certain implementations, the primary source table and the bowtie scatter source table can be generated by performing scatter simulations using a distributed model of the bowtie filter to determine the primary and scatter components of the X-ray beam at the virtual surface for a particular set of parameters for the X-ray source. Then for this set of parameters for the X-ray source, the tables can be used to provide the spatial, angular, and energy dependences of X-ray exiting from the virtual surface. Any known method can be used for the scatter simulation using the distributed model of the bowtie filter, including Monte Carlo methods, finite-element discrete ordinate methods, the RTE method described in method 200, or other RTE methods. Also, as discussed above, these simulations used to pre-calculate the lookup table can be performed using different resolution, convergence, and/or accuracy criteria than the subsequent repeated simulations of scatter for the object OBJ. If fine discretization is used for the lookup table, an RTE method is preferred over a Monte Carlo method for the scatter simulation because a Monte Carlo method would require the use of a large number of photons in order to reduce the statistical noise. The tables can be pre-calculated once before any CT scans of an object OBJ, and then used for every scan specific scatter simulation thereafter. Accordingly, the bowtie scatter simulation is not included in the time required for the scatter simulation of a scanned object OBJ.

Figure 6:
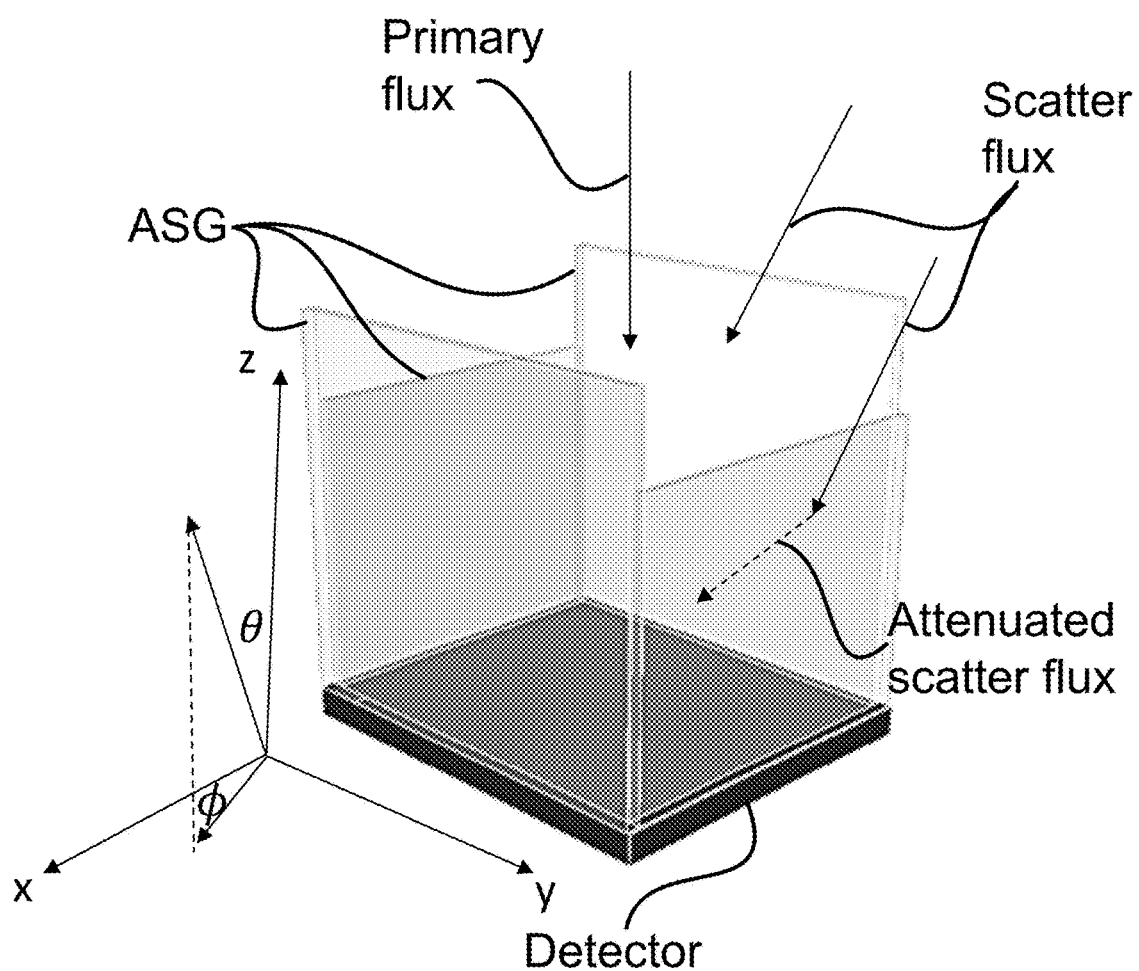
FIG. 6 shows a diagram of a geometry of an ASG to attenuate oblique-angle scatter, according to one implementation.

In addition to the simplification realized by using the bowtie source from the virtual surface, a table can also be generated to represent the scatter and attenuation due to ASG, which arranged between the object OBJ and the detectors, further simplifying and decreasing the computations and time for each scan-specific scatter simulation. FIG. 6 shows a diagram of an ASG. On the one hand, a ray of the primary flux is shown as being normal incident to the detectors, and, therefore, unobstructed by the walls of the ASG. On the other hand, the rays of the scatter flux are general oblique to the detectors, as represented in FIG. 6, and experience more attenuation than the rays of primary flux. How much more the scatter flux is attenuated depends on the geometry of the ASG and detector elements as well as details of the scatter flux.

Some of the scatter flux will be blocked an attenuated by the walls of the ASG, while other rays will reach the detectors. For example, more oblique angles of incidence for the scatter flux experience greater attenuation. Thus, a properly configured ASG can effectively reject a large percentage of the scatter flux. Of course, its effectiveness is determined by the dimension and material of ASG, which will be incorporated in to a realistic model/table representing the effect of the ASG on the incident X-rays. The methods described herein can use one or both of the two methods described below to obtain accurate and efficient scatter simulation of the ASG. These two ASG simulation methods are respectively referred to as the table method and the analytical method.

Regarding the table method, when the scatter flux passing through a wall of the ASG is partially transmitted through the wall an ASG table ($T_{ASG}(e, \theta, \phi)$) can be used to determine the amount of attenuation due to the ASG as a function of the incident angle of the scatter flux ($\varphi_{S,RTE}(r_D, e, \theta, \phi)$). That is, given the scatter flux $\varphi_{S,RTE}(r_D, e, \theta, \phi)$ incident on the ASG, the table values $T_{ASG}(e, \theta, \phi)$ can be used to determine the scatter flux $\varphi_{S,ASG}(r_D)$ incident on the detectors, which is given by $$\varphi_{S,ASG}(r_D) = \sum_E \sum_{\theta,\phi} \varphi_{S,RTE}(r_D, E, \theta, \phi) T_{ASG}(E, \theta, \phi).$$

As with the tables for the bowtie source, the ASG table can be generated via any known simulation method, including Monte Carlo, finite-element discrete ordinate, and RTE methods.

Regarding the analytical method, when the attenuation of scatter flux passing through ASG is approximately total, a simple analytical method can be used to determine geometrically whether the scatter flux strikes the wall or misses it. Based on the dimensions and positions of the grid walls in the ASG, the dimensions and positions of the detector elements, and the directions and positions of the rays of the scatter flux, a simple geometrical calculation can be used to determine whether the rays intersect with the grid walls, in which case the attenuation is regard as complete (i.e., $T_{ASG}=0$). Otherwise, there is no attenuation (i.e., $T_{ASG}=1$) and the ray reaches the detector unimpeded.

Having considered the simplifications of the bowtie filter and the ASG, attention is now turned to improving performance of the scatter simulation of the object OBJ. As discussed above, the basic idea of scatter correction is to remove the scatter flux from measured counts on the detectors to recover a signal purely representing the primary flux. When an RTE simulator is used, the scatter ($\varphi_{S,ASG}(r_D, vi)$) and primary ($\varphi_P(r_D,vi)$) flux distribution of each view (vi) can be simulated. Because the scatter distribution over views is low frequency (i.e., changes only gradually as a function of the view angle), the scatter incident on the detectors $\varphi_{S,ASG}(r_D, vi)$ can be simulated using a sparse-view mode and then scatter distributions for views in between the sparse simulated views can be interpolated. For example, method 200 can be used to perform the initial simulation of the sparse views. Further, as described below, method 200 can be used with any of three scatter correction methods described below (i.e., the multiplicative, additive, and kernel-based methods), or any combination of these three.

The multiplicative, additive, and kernel-based methods are each accelerated implementations of step 160 of method 100 because they can be performed more quickly than using method 200 to simulate the scatter at each view of a CT scan. This acceleration is accomplished by using method 200 to simulate scatter for some but not all of the views. Herein, the term "accelerated method" means a method that can used in combination with method 200 to simulate and correct for X-ray scatter over all views in a short time than it would take to simulate the X-ray scatter using method 200 only and then correct for X-ray scatter.

For example, in the multiplicative and additive methods scatter flux is first simulated for sparse views, and then the scatter flux for the remaining views can be interpolated from the sparse-view scatter flux. Interpolating can be performed very quickly, making the interpolation of the scatter flux over the remaining views quicker than using method 200 to simulate the scatter flux over the remaining views.

Figure 7A:
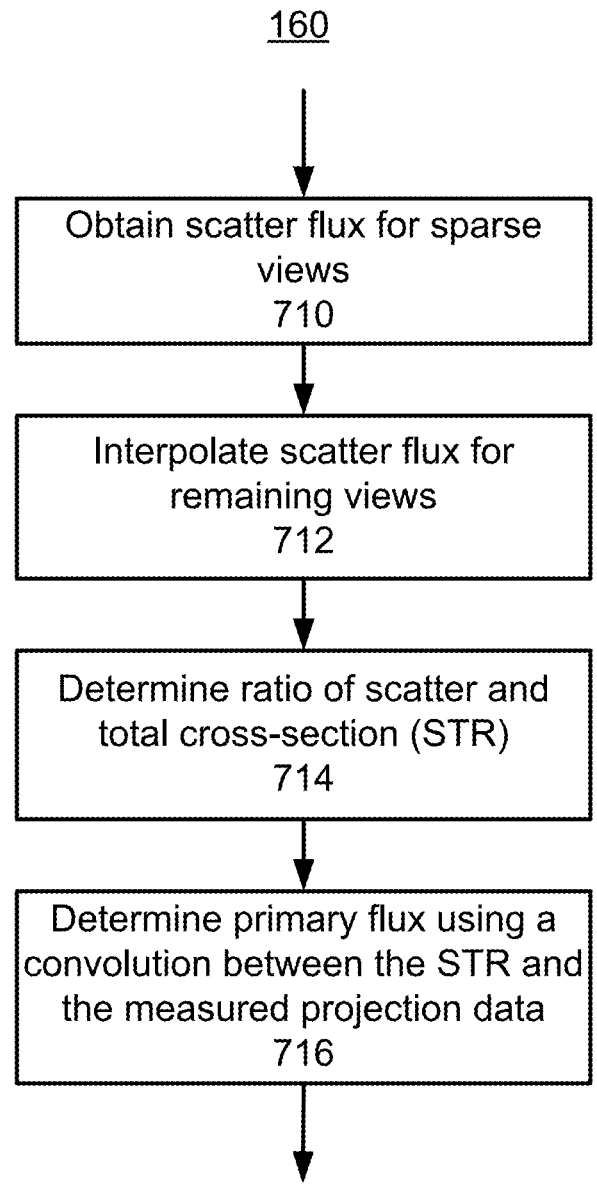
FIG. 7A shows a flow diagram of an example of a implementation for removing scatter flux from projection data to recover a primary flu using a multiplicative method, according to one implementation.
Figure 7B:
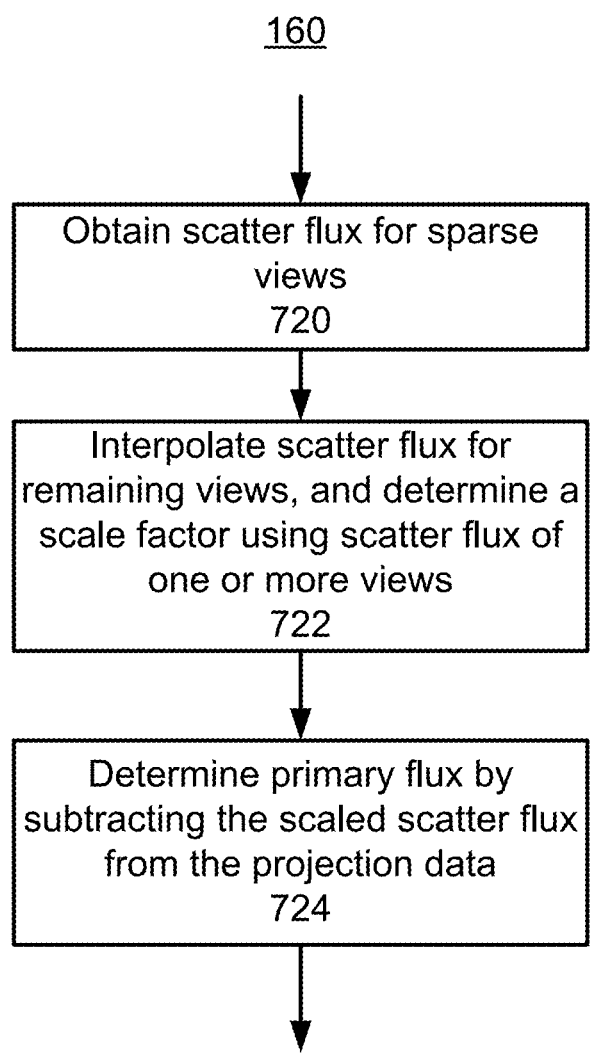
FIG. 7B shows a flow diagram of an example of an implementation for removing scatter flux from projection data to recover a primary flux using an additive method, according to one implementation.
Figure 7C:
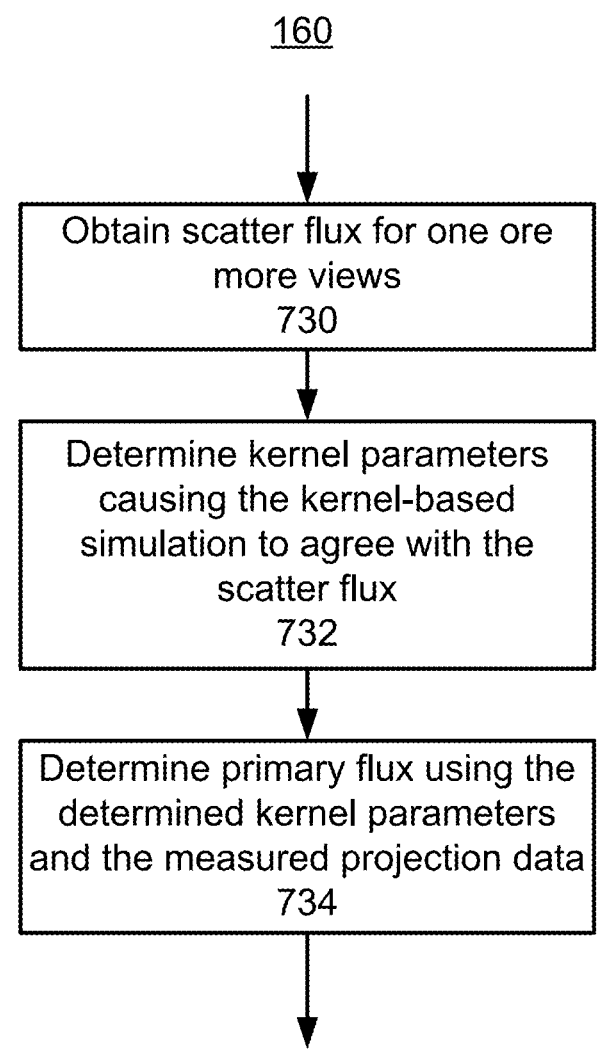
FIG. 7C shows a flow diagram of an example of an implementation for removing scatter flux from projection data to recover a primary flux using a kernel-based method, according to one implementation.

In the kernel-based method, scatter flux is simulated using method 200 for some views, and this scatter flux is used to train a kernel-based scatter simulation, which can be subsequently be used to determine the scatter flux for either all views or the remaining views. kernel-based scatter simulations can be fast compared to method 200. Flow diagrams of the multiplicative, additive, and kernel-based methods are shown in FIGS. 7A, 7B, and 7C, respectively.

Regarding the multiplicative method, for each view, the ratio of scatter and total flux STR($r_D$, vi) can be given by $$STR(r_D, vi)) = \frac{\varphi_{S,ASG}(r_D, vi)}{\varphi_{S,ASG}(r_D, vi) + \varphi_P(r_D, vi)}.$$

Using the ratio of scatter and total flux STR($r_D$, vi), the corrected measured total flux $\varphi_{C,M,T}(r_D, vi)$ can be calculated by the convolution $$\varphi_{C,M,T}(r_D,vi)=\varphi_{M,T}(r_D,vi)*(1-STR(r_D,vi)),$$

wherein $\varphi_{M,T}(r_D, vi)$ is the measured total flux. The scatter flux $\varphi_{S,ASG}(r_D,vi)$ used above to calculate the ratio of scatter and total flux STR($r_D$, vi) can be calculated using method 200 for all views. Alternatively, method 200 can be used to calculate the scatter flux $\varphi_{S,ASG}(r_D, vi)$ for sparse views, and then the remaining views can be interpolated from the simulated sparse views. An advantage of this method is that by using the convolution to determine the corrected measured total flux $\varphi_{C,M,T}(r_D, vi)$ negative values for the corrected measurements are avoided. Accordingly, this method is straightforward and robust.

FIG. 7A shows a flow diagram of one implementation of step 160 using the multiplicative method. In step 710, scatter flux corresponding a sparse views are obtained from step 150 of method 100. In step 712, scatter flux for the remaining views is interpolated from the sparse-views scatter flux. In step 714, the e ratio of scatter and total flux STR($r_D$, vi) is calculated. In an alternative implementation, the order of steps 712 and 714 can be reversed and the STR can be calculated for the sparse views and then the STR for all views can be interpolated from the STR over the sparse views. In step 714, the convolution is used to calculate the corrected measured total flux $\varphi_{C,M,T}(r_D, vi)$ from the $\varphi_{M,T}(r_D, vi)$ is the measured total flux and the ratio of scatter and total flux STR($r_D$, vi).

The additive method has other benefits over the multiplicative method described above. For example, the multiplicative method can disadvantageously change the noise pattern of the measurements, affecting imaging quality when iterative reconstruction is performed using the corrected measured total flux $\varphi_{C,M,T}(r_D,vi)$. In contrast, the additive method does not change the noise pattern. Rather, the additive method uses a scale factor to calibrate the interpolation from the simulated scatter flux. That is, a scale factor $\alpha$ is used between the simulated and measured flux. For example, the scale factor $\alpha$ can be determined empirically using measured calibration methods before the CT scan. After $\alpha$ is obtained, $\varphi_{C,M,T}(r_D, vi)$ can be calculated using the expression given by $$\varphi_{C,M,T}(r_D,vi)=\varphi_{M,T}(r_D,vi)-\alpha\varphi_{S,ASG}(r_D,vi).$$

Like the multiplicative method, the additive method can also use method 200 to simulate the scatter flux for all views, or to simulate the scatter flux for only sparse views and then interpolate the scatter flux for the remaining views.

FIG. 7B shows a flow diagram of one implementation of step 160 using the additive method. In step 720, scatter flux corresponding a sparse views are obtained from step 150 of method 100. In step 722, scatter flux for the remaining views is interpolated from the sparse-views scatter flux. Further in step 722, the scale factor $\alpha$ is determined by comparing the simulated and measured flux. In step 724, the scale factor $\alpha$ is applied to the scatter flux for all views, and after scaling the scatter flux is subtracted from the measured projection data to recover the primary flux.

The kernel-based method has the advantages of being both simple and highly efficient. A disadvantage of conventional kernel-based methods is the reduced accuracy and added complexity arising from the calibration of the parameters used in the kernel, which often requires extra calibration steps involving experiments performed on a simple phantom prior to the CT scan of the object.

For example, one kernel-based model uses a double Gaussian kernel $$G_2(x,y)=A_1 \exp[-\alpha_1(x^2+y^2)]+A_2\exp[-\alpha_2(x^2+y^2)],$$

wherein the first term (i.e., with the coefficient $A_1$) models the Rayleigh scattering, and the second term (i.e., with the coefficient $A_2$) models the Compton scattering. In this forward-scatter model, the scattered radiation S(x, y) is given by $$S(x,y)=SF(P(x,y))*G_2(X,y),$$

wherein the scattering function is expressed as $$SF(X) = -X \log(X).$$

In the double Gaussian kernel, the constants $A_1$, $A_2$, $a_1$, and $a_2$ can be calibrated using a phantom.

FIG. 7C shows a flow diagram of one implementation of step 160 using the kernel-based method. In step 730, scatter flux corresponding a few views are obtained from step 150 of method 100. In step 732, the kernel parameters are updated to achieve agreement between the scatter simulation using the kernel-based method and the scatter flux obtained at step 730. In step 734, the kernel-based method using the updated kernel parameters is applied to the measured projection data to recover the primary flux.

Simulations using method 200 can replace certain calibrations and improve the accuracy of kernel-based scatter correction. In certain implementations, the scatter correction performance is improved by training kernel-based method using RTE simulation results in a few views to better optimize the empirically derived parameters, such as the coefficients $A_1$, $A_2$, $a_1$, and $a_2$ in the double Gaussian kernel provided as an example above. In certain implementations, the kernel-based method can be trained using scatter simulations obtained using an RTE method (e.g., method 200). The scatter simulation results can be obtained at a few views, and then the parameters of the kernel can be adjusted to minimize a cost function, e.g., to find a solution of the expression $$p(v) = \operatorname*{argmin}_{p(v)} \sum_{vi} \sum_{dj} \|\varphi_{S,ASG}(dj, vi) - \varphi_{k,S,ASG}(dj, vi, p(vi))\|_2 + \lambda U(p(vi)),$$

wherein $\varphi_{k,S,ASG}(dj, vi, p(vi))$ is the scatter flux via kernel method, p (v) is the open parameters for scatter kernel, and $\lambda U(p(vi))$ is a penalty term. Any suitable kernel, such as double Gaussian kernel, can be used for this method. After p(v) is determined, the trained kernel method can then be used for further scatter correction for other views within the scan, or even for other scans.

Figure 8:
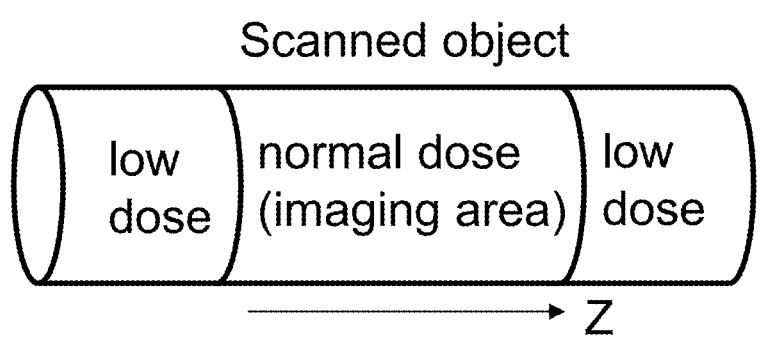
FIG. 8 shows a diagram of a scanning geometry with a normal dose in an imaging region and a low dose of X-ray radiation in surrounding regions, according to one implementation.

Now an implementation is discussed to account for scatter flux from the object OBJ for regions outside of an image region. For example, this can occur when a narrow field of view (FOV) is selected during repeated imaging, such as during an image-guided surgical procedure, to reduce the radiation dose. FIG. 8 shows a scanned object OBJ for a case in which only a portion of the object OBJ is being imaged. To keep the radiation exposure to a patient as low as reasonably possible, only a normal dose of radiation is used within the imaging area. However, scatter from the image area can reach regions of the object OBJ outside of the imaging area, and can then be re-scattered for these non-imaging areas to the detectors. Accordingly, a complete model of the scatter flux will account for scattering both inside and outside the imaging area.

For example, for current CT geometries and applications, a patient can be exposed to multiple CT scans/image or to imaging over a long period of time, as in a CT profusion study or an image guided medical procedure. Thus, the FOV might be reduced to reduce the radiation dose to the patient. However, as discussed above, the detectors can still be exposed to and collect scatter flux from the non-imaging area, i.e., outside of the FOV for the scan. To account for this scatter outside of the FOV, an over-scan protocol can be used to acquire projection data at a lower dose outside of the imaging volume, and this lower dose projection data can be used to reconstruct an image of the scanned object outside the imaging area, thereby improving the model for the scatter simulation. That is, as shown in FIG. 8, a low dose region is designated to the sides of the imaging area.

Further, in certain implementations, the scatter simulation can be improved by using atlas information to expand the image volume along the z direction either with or without using additional low-dose scanning around the imaging area. To illustrate, even without low dose irradiation to the sides of the imagining area, a priori knowledge of anatomy can enable extrapolation of likely attenuation density and scattering properties for tissues lying to either side of the imagining area.

Another alternative, which can be used together with or instead of the options described above, is to use whole-body scout scanning information to develop a more complete model of the object OBJ. For example, in a long procedure using CT or fluoroscopic imaging, such as in a surgery or profusion study, an initial CT image of the whole body could be used for simulating the scatter, even after the field of view has been narrowed to limit the radiation dose to the patient.

Further, the RTE scatter simulation can be further improved by segmenting the reconstructed image of patient into different organs. As mentioned above, material decomposition based on spectral resolved projection data can be used for this process, but segmenting into organs can also be performed for CT projection data using energy integrating detectors, rather than or in addition to energy-resolving detectors. For example, a simple HU threshold can be used to segment a reconstructed image.

Consider a reconstructed image in which the voxel at position x and y is given by HU (x, y). Regions of the reconstructed image HU (x, y) can be decomposed into two or more material components. In certain implementations, a spatial function describing the aggregated X-ray attenuation for a combination of material 1 and material 2 can be respectively given in Hounsfield units by the function HU (x, y). Then the reconstructed image HU (x, y) can be segmented into two component images $c_1(x,y)$ and $c_2(x,y)$ according to the expressions $$c_1(x, y) = \begin{cases} \dfrac{HU(x, y) + 1000}{HU_1 + 1000} & HU(x, y) < HU_1 \\ \dfrac{HU(x, y) - HU_1}{HU_2 - HU_1} & HU_1 \leq HU(x, y) \leq HU_2, \text{ and} \\ 0 & HU(x, y) > HU_2 \end{cases}$$

$$c_2(x, y) = \begin{cases} 0 & HU(x, y) < HU_1 \\ \dfrac{HU(x, y) - HU_1}{HU_2 - HU_1} & HU_1 \leq HU(x, y) \end{cases}.$$

The constants $HU_1$ and $HU_2$ are respective thresholds representing a transition from being completely the first material component to a mixed material, and then from being a mixed material to being completely the second material. Different scattering properties can then be attributed to the different material components.

In certain implementations, the acquired images in the non-imaging regions might have poor imaging quality, due to scatter-flux contamination and low dose in non-imaging regions. Consequently, in the HU threshold method being less effective in the non-imaging regions. Accordingly, it might only be possible to segment these regions into a few components such as air, soft tissue, and bone, rather than into a greater number of material components. On the other hand, in regions with a sufficiently high signal-to-noise ratio, soft tissue can be further classified using, e.g., advanced segmentation strategies such as those incorporating atlas-aided methods in order to partition and subdivide the soft-tissue regions into particular types of soft tissue thereby to enable more accurate scatter simulations accounting for different scatter cross-sections variously associated with the types of soft tissue.

As discussed above, the methods described herein provide several advantages over other scatter simulation and correction methods. The the methods described herein provide efficient mechanisms to account for the effects of the unchanging elements in a scan, such as the bowtie filter and the ASG. The methods described herein provide a new method/framework for scatter correction of CT projection data using an RTE simulation, which among other things, is better able to handle complex geometry and multiple materials and perform patient-specific scatter correction.

The methods described herein provide several advantages with respect to efficiency and accuracy, especially when the methods described herein are contrasted with pure convolution methods. In contrast with Monte Carlo (MC) methods, the methods described herein provide scatter simulations free from shot noise. In contrast to other RTE-based methods, the methods described herein do not require two-pass scatter correction. Also, as described above, the methods described herein provide a novel scanning protocol to account for scatter extending into an a non-imaging region to correct for scatter rebounding from the non-imaging region into the detectors.

Figure 9:
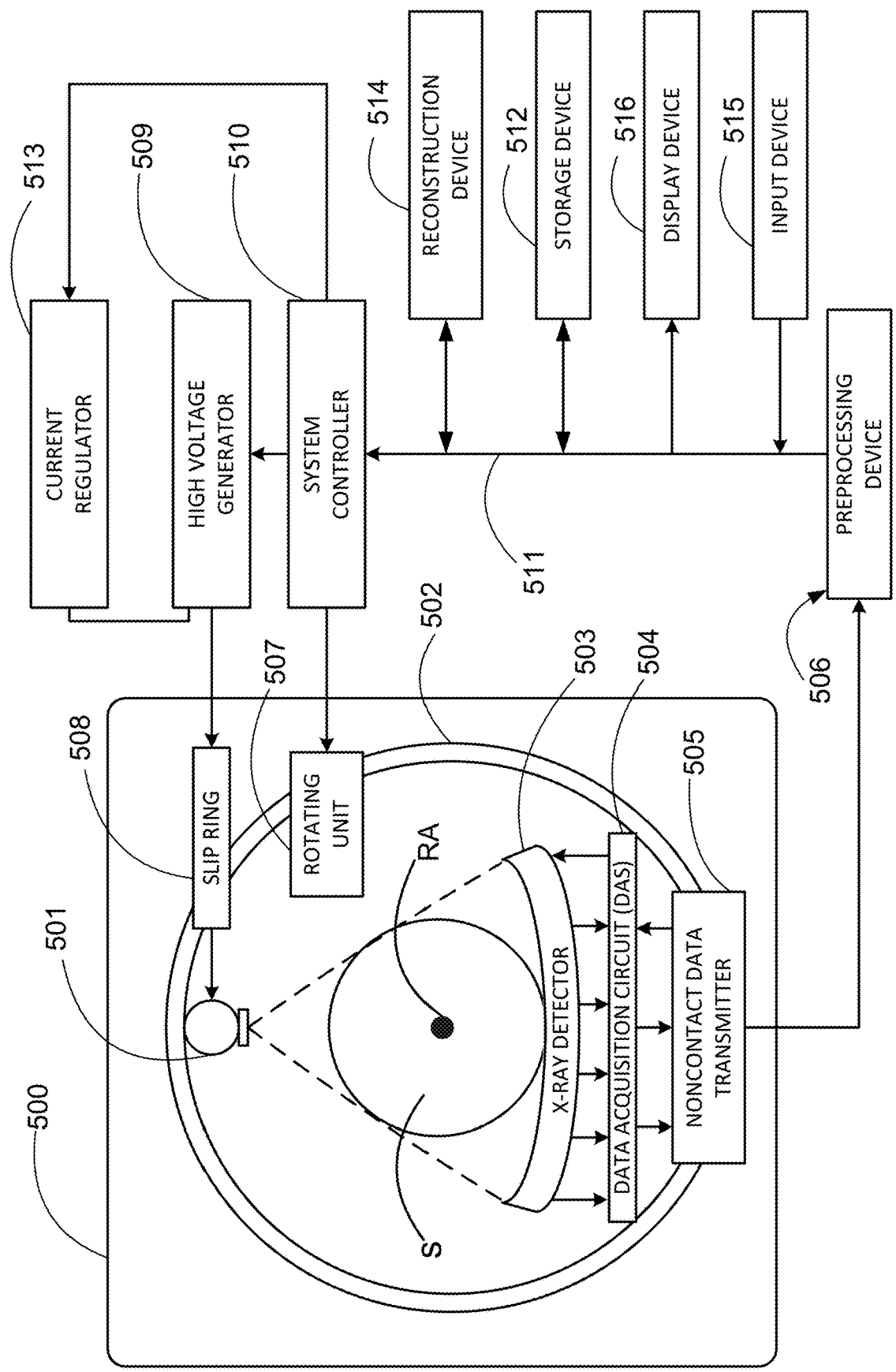
FIG. 9 shows a schematic of an implementation of a CT scanner.

FIG. 9 illustrates an implementation of the radiography gantry included in a CT apparatus or scanner. As shown in FIG. 9, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross-sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing the CT image reconstruction, material decomposition, and scatter estimation and corrections methods including methods 100 and 200 discussed herein.

The reconstruction device 514 can execute the methods 100 and 200 discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can be performed using filtered back projection, iterative image reconstruction methods, or stochastic image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain projection data representing an intensity of X-ray radiation transmitted through an object and detected at a plurality of detector elements, the projection data being obtained for a plurality of views corresponding to respective projection angles relative to the object,
reconstruct, using the projection data, an image of the object to generate a spatial model of scatter of the X-ray radiation from the object,
simulate, for one or more views of the plurality of views, a scatter flux of the one or more views representing an intensity of scattered X-ray radiation detected at the plurality of detector elements, the intensity of scattered X-ray radiation being determined using a radiative transfer equation (RTE) method based on integrating a radiative transfer equation, and
determine, using the simulated scatter flux of the one or more views together with an accelerated method, which is accelerated relative to the RTE method, primary flux of the plurality of views, the primary flux representing an intensity of X-rays that have not been scattered, which are incident on the plurality of detector elements, wherein
a combination of simulating the scatter flux of the one or more views using the RTE method together with determining of the primary flux using the accelerated method is quicker than a method determining the primary flux using the RTE method to simulate scatter flux for all views of the plurality of views.

2. The apparatus according to claim 1, wherein the circuitry is further configured to determine the primary flux by
simulating, using the accelerated method, which is based on the scatter flux of the one or more views, a scatter flux of remaining views representing an intensity of scattered X-ray radiation detected at the plurality of detector elements for remaining views of the plurality of views other than the one or more views, and
removing, from the projection data, the scatter flux of the one or more views and the scatter flux of the remaining views to generate the primary flux.

3. The apparatus according to claim 1, wherein the circuitry is further configured to reconstruct, using the primary flux, another image of the object.

4. The apparatus according to claim 3, wherein the circuitry is further configured to
generate, using the another image, another spatial model of the scatter of X-ray radiation from the object,
repeat the simulating of scatter flux of the one or more views, but using the another spatial model instead of the spatial model, to generate another scatter flux of the one or more views, and
repeat the determining of the primary flux of the plurality of views, but use the another scatter flux of the one or more views instead of the scatter flux of the one or more views.

5. The apparatus according to claim 1, wherein the circuitry is further configured to reconstruct the image of the object by
correcting, using a scatter-simulation method, the projection data to remove scatter and generate corrected projection data, and
reconstructing the image using the corrected projection data together with a computed-tomography image-reconstruction method.

6. The apparatus according to claim 1, wherein the circuitry is further configured to generate the spatial model of scatter of the X-ray radiation from the object by
segmenting the image into a plurality of regions corresponding to material components, and
assigning each region of the plurality of regions an energy-dependent scatter cross-section based of a material component corresponding to the region.

7. The apparatus according to claim 6, wherein the circuitry is further configured to perform the segmenting of the image using one or more of information of an amplitude of total X-ray attenuation at respective pixels or voxels of the reconstructed image, information of energy dependence of the X-ray attenuation at the respective pixels or voxels of the reconstructed image, and anatomical information.

8. The apparatus according to claim 1, wherein the circuitry is further configured to generate the spatial model of scatter of the X-ray radiation from the object by extrapolating a model of X-ray scatter from the object outside of an imaging region of the CT scanner.

9. The apparatus according to claim 8, wherein the circuitry is further configured to perform the step of extrapolating the model of X-ray scatter from the object outside of the imaging region of the CT scanner by using one or more of a low-dose reconstructed image of a part of the object outside of the imaging region, anatomical information, and a reconstructed image from a prior CT scan.

10. The apparatus according to claim 1, wherein the circuitry is further configured to perform the step of determining of the primary flux using the accelerated method, wherein the accelerated method is one of a multiplicative method, an additive method, and a kernel based method,
the multiplicative method including
interpolating a scatter flux of remaining views based on the scatter flux of the one or more views to generate a scatter flux of all views of the plurality of views, the remaining views being views of the plurality of views other than the one or more views,
determining, using the scatter flux of the all views, a ratio of scatter flux to total flux, and
convolving the projection data with a difference between unity and the ratio of scatter flux to total flux to generate the primary flux of the plurality of views,
the additive method including
interpolating the scatter flux of the remaining views of the plurality of views from the scatter flux of the one or more views to generate the scatter flux of the all views,
determining a scale factor between empirically measured scatter flux and the scatter flux of the one or more views, and
determining the primary flux using a difference between the projection data and a product of the scale factor and the scatter flux of the all views, and
the kernel-based method including
modifying a parameter of a kernel based on the scatter flux of the one or more views, and
determining, using the kernel with the modified parameter, scatter flux of the remaining views to generate the scatter flux of the all views, wherein
the remaining views of the plurality of views include views other than the one or more views.

11. A computed tomography (CT) scanner, comprising:
a gantry having an opening in which an object can be placed;
an X-ray source fixed to a rotatable member of a gantry of the CT scanner and irradiating X-ray radiation;
an X-ray detector comprising a plurality of detector elements, the X-ray detector being fixed to the rotatable member and arranged across the opening of the gantry and diametrically opposed to the X-ray source; and
the circuitry according to claim 1.

12. An apparatus, comprising:
a memory storing pre-calculated scatter values representing angle-dependent scatter for X-ray radiation from a first part of a computed tomography (CT) scanner, the first part being arranged to have a position and orientation that is constant relative to an X-ray source of the CT scanner, when the CT scanner is rotated according to a plurality of views; and
circuitry configured to
obtain projection data representing an intensity of X-ray radiation transmitted from the X-ray source, through an object, and detected at a plurality of detector elements of the CT scanner, the projection data being obtained for the plurality of views, which correspond to respective projection angles of the X-ray source relative to the object,
reconstruct, using the projection data, an image of the object to generate a spatial model of scatter of X-ray radiation from the object,
simulate, for one or more views of the plurality of views, a scatter flux of the one or more views representing an intensity of scattered X-ray radiation detected at the plurality of detector elements, the scatter flux of the one or more views being simulated using a scatter simulation method that uses the pre-calculated scatter values to simulate a scatter flux from the first part, and
determine, using the simulated scatter flux of the one or more views and a scatter simulation method, primary flux of the plurality of views, the primary flux representing an intensity of X-rays that have not been scattered, which are incident on the plurality of detector elements, wherein
the circuitry is further configured to simulate the scatter flux of the one or more views using the pre-calculated scatter values to simulate the scattering by the first part, wherein the first part is one of a filter and an anti-scatter grid.

13. The apparatus according to claim 12, wherein the circuitry is further configured to simulate the scatter flux of the one or more views using the RTE method, wherein the RTE method includes
integrating an attenuation from the X-ray source to a detection location or a first scatter location to generate a primary flux,
integrating the primary flux at the scatter location with a predefined scatter cross-section at the first scatter location to generate a first-scatter flux, which includes a plurality of first-scatter spherical-harmonic components, and
iteratively updating a multiple-scatter flux, which is decomposed into a plurality of multiple-scatter spherical-harmonic components, by integrating products of respective spherical-harmonic components of a previous iteration of the multiple-scatter flux at a scatter location of the previous iteration with corresponding spherical-harmonic components of the predefined scatter cross-section at a scatter location of a next iteration to generate the multiple-scatter flux of the next iteration, and the multiple-scatter flux of a first iteration is the first-scatter flux and a scatter location of the first iteration is the first scatter location.

14. The apparatus according to claim 12, wherein the circuitry is further configured to simulate the scatter flux of the one or more views using another pre-calculated scatter values representing scatter of X-ray radiation from a second part of the CT scanner, wherein the first part is a filter and the second part is an anti-scatter grid.

15. The apparatus according to claim 12, wherein the circuitry is further configured to determine the pre-calculated scatter values by
determining, based on a geometry of the anti-scatter grid and a trajectory of a ray of X-ray radiation, whether the ray intersects with the anti-scatter grid, and
determining that X-ray radiation having the trajectory of the ray does not reach the plurality of detector elements, when the ray intersects with the anti-scatter grid.

16. The apparatus according to claim 12, wherein the circuitry is further configured to determine the pre-calculated scatter values by simulating the scatter flux from the first part using one of a Monte Carlo method and an RTE-based method and by using parameters of a geometry of the first part and predefined scatter cross-sections for material components of the first part.

17. The apparatus according to claim 12, wherein the circuitry is further configured to simulate the scatter flux of the one or more views using the pre-calculated scatter values together with a radiative transfer equation (RTE) method based on integrating a radiative transfer equation, simulate, using the pre-calculated scatter values together with an accelerated method that uses the simulated scatter flux of the one or more views, a scatter flux of remaining views, the remaining views being views of the plurality of views other than the one or more views, and the accelerated method simulating the scatter flux of remaining views more quickly than the RTE method, and remove, from the projection data, the scatter flux of the one or more views and the scatter flux of the remaining views to generate the primary flux.

18. A method, comprising:

obtaining projection data representing an intensity of X-ray radiation transmitted through an object and detected at a plurality of detector elements, the projection data being obtained for a plurality of views corresponding to respective projection angles relative to the object, reconstructing, using the projection data, an image of the object to generate a spatial model of scatter of the X-ray radiation from the object, simulating, for one or more views of the plurality of views, a scatter flux of the one or more views representing an intensity of scattered X-ray radiation detected at the plurality of detector elements, the intensity of scattered X-ray radiation being determined using a radiative transfer equation (RTE) method based on integrating a radiative transfer equation, and determining, using the simulated scatter flux of the one or more views and an accelerated method, which is accelerated relative to the RTE method, primary flux of the plurality of views, the primary flux representing an intensity of X-rays that are incident on the plurality of detector elements without being scattered, wherein a combination of simulating the scatter flux of the one or more views using the RTE method together with determining of the primary flux using the accelerated method is quicker than a method determining the primary flux using the RTE method to simulate scatter flux for all views of the plurality of views.

19. A non-transitory computer-readable storage medium storing executable instructions, wherein the instructions, when executed by circuitry, cause the circuitry to perform the method according to claim 18.

* * * * *